(12) United States Patent
Apte-Deshpande et al.

(10) Patent No.: US 10,058,589 B2
(45) Date of Patent: Aug. 28, 2018

(54) STABLE PHARMACEUTICAL COMPOSITION OF ETANERCEPT IN A PHOSPHATE CITRATE BUFFER WITH GLYCINE AS AN ANTI-AGGREGATING AGENT

(71) Applicant: LUPIN LIMITED, Mumbai, Maharashtra (IN)

(72) Inventors: Anjali Deepak Apte-Deshpande, Maharashtra (IN); Vaibhav Dyaneshwar Deokar, Maharashtra (IN); Rustom Sorab Mody, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/438,404

(22) PCT Filed: Oct. 24, 2013

(86) PCT No.: PCT/IB2013/059612
§ 371 (c)(1),
(2) Date: Apr. 24, 2015

(87) PCT Pub. No.: WO2014/064637
PCT Pub. Date: May 1, 2014

(65) Prior Publication Data
US 2015/0283241 A1 Oct. 8, 2015

(30) Foreign Application Priority Data

Oct. 26, 2012 (IN) ............................ 1235/KOL/2012
Oct. 26, 2012 (IN) ............................ 1236/KOL/2012

(51) Int. Cl.
*C07K 14/715* (2006.01)
*C07K 19/00* (2006.01)
*A61K 38/17* (2006.01)
*A61K 9/00* (2006.01)
*A61K 9/19* (2006.01)

(52) U.S. Cl.
CPC ........ *A61K 38/1793* (2013.01); *A61K 9/0019* (2013.01); *A61K 9/19* (2013.01); *C07K 14/715* (2013.01); *C07K 19/00* (2013.01); *C07K 2319/30* (2013.01)

(58) Field of Classification Search
None
See application file for complete search history.

(56) References Cited

U.S. PATENT DOCUMENTS 5,215,743 A 6/1993 Singh et al.
6,923,956 B1 * 8/2005 Tschope ............... A61K 38/215
424/85.6
7,648,702 B2 1/2010 Gombotz et al.
2007/0053906 A1 3/2007 Samaritani et al.
2010/0278822 A1 * 11/2010 Fraunhofer ......... A61K 39/39591
424/133.1

FOREIGN PATENT DOCUMENTS

WO 2011/141926 A2 11/2011
WO 2012/065072 A2 5/2012

OTHER PUBLICATIONS

Glycine. (Jun. 6, 2016). In Wikipedia, The Free Encyclopedia. Retrieved 02:36, Jun. 17, 2016, from https://en.wikipedia.org/w/index.php?title=Glycine&oldid=724002695.*
McIlvaine buffer. (Sep. 16, 2015). In Wikipedia, The Free Encyclopedia. Retrieved 20:05, Jun. 16, 2016, from https://en.wikipedia.org/w/index.php?title=McIlvaine_buffer&oldid=681258150.*
Nayar et al. High throughput formulation: strategies for rapid development of stable protein products. Pharm Biotechnol. 2002;13:177-98.*
Carpenter et al. Rational design of stable lyophilized protein formulations: theory and practice. Pharm Biotechnol. 2002;13:109-33.*
Chirality. (May 7, 2017). In Wikipedia, The Free Encyclopedia. Retrieved 21:43, May 15, 2017, from https://en.wikipedia.org/w/index.php?title=Chirality&oldid=779121850.*
Lowe et al. Aggregation, stability, and formulation of human antibody therapeutics. Adv Protein Chem Struct Biol. 2011;84:41-61.*
International Search Report (PCT/ISA/220) dated Mar. 19, 2014 for corresponding International Patent Application No. PCT/IB2013/059612, filed Oct. 24, 2013.
Written Opinion (PCT/ISA/237) dated Mar. 19, 2014 for corresponding International Patent Application No. PCT/IB2013/059612, filed Oct. 24, 2013.
Kita et al., "Salts and Glycine Increase reversibility and Decrease Aggregation during Thermal Unfolding of Ribonuclease-A.", Bioscience, Biotechnology, and Biochemistry, vol. 66, No. 4, Jan. 1, 2002 (Jan. 1, 2002), pp. 880-882, XP055092739, ISSN: 0916-8451, DOI: 10.1271/bbb.66.880.
Anonymous: "Enrbel, INN etanercept", European Medicines Agency, Sep. 11, 2009 (Sep. 11, 2009), pp. 184-185, XP002717733, Retrieved from the Internet: URL: http://www.ema.europa.eu/docs/en_GB/document_library/EPAR_-_Product_Information/human/000262/WC500027361.pdf.
Hohmann et al., "Two Different Cell Types Have Different Major Receptors for Human Tumor Necrosis Factor (TNFα)*", The Journal of Biological Chemistry, vol. 264, No. 25, Issue Sep. 5, 1989, pp. 14927-14934.

(Continued)

*Primary Examiner* — Zachary C Howard
(74) *Attorney, Agent, or Firm* — Merchant & Gould P.C.

(57) ABSTRACT

The present invention relates to the stable pharmaceutical compositions comprising tumor necrosis factor receptor Fc fusion protein (TNFR:Fc). More particularly, it relates to the stable pharmaceutical compositions comprising tumor necrosis factor receptor Fc fusion protein (TNFR:Fc), phosphate-citrate buffer. It also relates to the methods of manufacturing the composition, method of administration and kits containing the same.

7 Claims, No Drawings

(56) References Cited

OTHER PUBLICATIONS

Brockhaus et al., "Identification of two types of tumor necrosis factor receptors on human cell lines by monoclonal antibodies", Immunology, Proc. Natl. Acad. Sci. USA, vol. 87, Apr. 1990, pp. 3127-3131.

* cited by examiner

STABLE PHARMACEUTICAL COMPOSITION OF ETANERCEPT IN A PHOSPHATE CITRATE BUFFER WITH GLYCINE AS AN ANTI-AGGREGATING AGENT

FIELD OF INVENTION

The invention provides stable pharmaceutical compositions comprising tumor necrosis factor receptor Fc fusion protein (TNFR:Fc). The invention also provides methods of manufacturing the composition, method of administration and kits containing the same.

BACKGROUND OF INVENTION

Tumor necrosis factor (TNF) alpha is a cytokine that promotes the inflammation and its associated signs by binding to its receptor. It is produced by macrophages and many other immune cells. It is involved in pathogenesis of many inflammatory disorders like rheumatoid arthritis, psoritic arthritis, SLE, Crohn's disease etc. Hohmann et al (Hohmann et al. 1989 *J Biol Chem.* 25, 14927-34) identified 2 distinct receptors of TNF-alpha which are present on different cell types viz. myeloid cells and epithelial cells. Using monoclonal antibodies, Brockhaus et al (Brockhaus et al. 1990 *Proc Natl Acad Sci U S A.*, 87(8), 3127-31) demonstrated that both TNF-alpha and beta bind to both the receptors with high affinity.

Tumor necrosis factor-alpha (TNF-alpha) is a central regulator of inflammation, and TNF-alpha antagonists may be effective in treating inflammatory disorders in which TNF-alpha plays an important pathogenetic role. Inhibition of TNF has proven to be an effective therapy for patients with rheumatoid arthritis and other forms of inflammatory disease including psoriasis, psoriatic arthritis, and ankylosing spondylitis, inflammatory bowel disease. One such TNF-alpha antagonist is Etanercept.

Etanercept is a dimeric fusion protein produced by recombinant DNA technology where gene of soluble, ligand binding portion of TNF receptor 2 is fused with gene of Fc component of human IgG1 to give the desired fusion protein (U.S. Pat. No. 7,648,702). Etanercept is expressed in CHO cells. The Fc component of Etanercept lacks CH1 domain but has CH2, CH3 domains and hinge region. The fusion protein has approximate molecular weight of 150 kD and consists of 934 amino acids. Etanercept interferes with TNF and acts as a TNF inhibitor due to which it can be used as a biopharmaceutical to treat autoimmune diseases. It prevents progressive destruction of joints in patients with rheumatoid arthritis and the arthritis of psoriasis.

Due to its unique structure, Etanercept binds 50-100 folds more efficiently to TNF alpha than its endogenous receptor (Gofeeet al. 2003 *J Am Acad Dermatol.* 49, S105-111, Strober 2005 *Semin Cutan Med Surg.* 24; 28-36). Additionally, due to its dimeric nature it can bind to 2 TNF alpha molecules as compared to one bound by endogenous receptor. Conjugation of this molecule to Fc region of IgG increases the half life as compared to endogenous soluble form. Commercially, Etanercept is available in both Lyophilized and liquid forms.

The most important feature of a composition is to help the protein to retain its structural conformation or its activity. The stability of protein in a composition can be related with long-term storage. It is understood to mean that the active polypeptide of the pharmaceutical composition does not substantially lose its activity as compared to the composition at the beginning of storage.

All polypeptides have an Isoelectric Point (pI), which is generally defined as the pH at which a polypeptide carries no net charge. It is known in the art that protein solubility is typically lowest when the pH of the solution is equal to the isoelectric point (pI) of the protein.

The Tm of the Fab domain of a protein is a good indicator of the thermal stability of a protein and may further provide an indication of the shelf-life. Tm values of proteins determined by differential scanning calorimetry, give insight into heat-induced changes in protein conformation, mechanisms of protein unfolding and stabilization in solution. A lower Tm indicates less stability of a protein in given solution, whereas a higher Tm indicates a better stability of the protein. The Tm of the protein will vary based on the formulation composition which in turn reflects its stability in respective formulation.

During long term storage, both aqueous and lyophilized compositions of proteins can lose active protein due to aggregation or degradation. Aggregation of the protein can lead to immunogenicity and is undesirable. Since the concentration of Etanercept used in the composition is high, there is a likely possibility of protein aggregation during long term storage. To improve the stability of the protein either the concentration of the existing excipients can be varied or new excipients can be added to modify the composition.

U.S. Pat. Nos. 5,215,743; 7,648,702; US application US 20070053906 and WO 2011141926 disclose pharmaceutical compositions comprising aqueous composition of TNF-binding protein comprising a TNF-binding protein, a buffer and an isotonicity agent.

SUMMARY OF THE INVENTION

In an embodiment, the invention is related to a stable pharmaceutical composition comprising TNFR:Fc fusion protein and phosphate-citrate buffer.

In another embodiment, the invention is related to a stable pharmaceutical composition comprising TNFR:Fc fusion protein, phosphate-citrate buffer and anti-aggregating agent selected from L-glycine, urea and 2-hydroxypropyl beta-cyclodextrin (HPBCD).

In another embodiment, the invention is related to a stable pharmaceutical composition comprising TNFR:Fc fusion protein, phosphate-citrate buffer, anti-aggregating agent selected from L-glycine, urea and HPBCD, a tonicity modifying agent and a stabilizing agent.

In yet another embodiment, the invention is related to the method of treating a disease using the stable pharmaceutical composition of the present invention. The disease may be rheumatoid arthritis, polyarticular juvenile idiopathic arthritis, psoriatic arthritis, ankylosing spondylitis or plaque psoriasis.

In another embodiment the invention is related to a kit or container containing the pharmaceutical composition of the invention.

The details of one or more embodiments of the invention set forth below are illustrative only and not intended to limit to the scope of the invention. Other features, objects and advantages of the inventions will be apparent from the description and claims.

DETAIL DESCRIPTION OF INVENTION

The invention provides a stable pharmaceutical composition comprising TNFR molecules fused to an Fc portion of a human immunoglobulin (TNFR:Fc fusion protein). More particularly, the invention relates to the stable pharmaceutical composition of etanercept in phosphate-citrate buffer, which displays a lower degradation potential. In an embodiment of the invention, the TNFR:Fc fusion protein is etanercept.

It has been reported in U.S. Pat. No. 7,648,702 patent and WO2011141926 application that the pharmaceutical compositions of Etanercept using L-glycine as anti-aggregating agent in phosphate buffer are not stable as compared to the compositions of etanercept with other amino acid such as arginine, proline, lysine, aspartic acid as anti-aggregating agent in phosphate buffer. The WO2011141926 application discloses that the composition comprising Etanercept in phosphate buffer and L-glycine as anti-aggregating agent showed aggregation as well as fragmentation products.

While studying the Etanercept compositions in different buffers and using different anti-aggregating agents it was observed that Etanercept composition comprising phosphate-citrate buffer with L-glycine as anti-aggregating agent showed improved stability as compared to Etanercept composition comprising phosphate buffer with L-glycine as anti-aggregating agent at 5° C. and 40° C.

As illustrated in the example section, the stability of Etanercept composition essentially consisting of phosphate-citrate buffer in combination with L-glycine as anti-aggregating agent were assessed during a 6 months stability study at 5° C. as well as 2 weeks study at 40° C. (stress conditions stability studies). Compositions comprising the phosphate-citrate buffer system were determined to be superior as compared to composition comprising phosphate buffer system with respect to the % aggregation products and & degradation products as determined by SEC.

The stable pharmaceutical composition used herein means that the TNFR:Fc fusion protein exhibits following features:

i. The stable pharmaceutical composition of TNFR:Fc fusion protein in phosphate-citrate buffer exhibits improved stability as compared to the composition of etanercept comprising phosphate buffer, arginine and sodium chloride. The % aggregates are less in the Etanercept composition comprising L-glycine as anti-aggregating agent in phosphate-citrate buffer as determined after 2 weeks of storage at 40° C. by SEC.

ii. The stable pharmaceutical composition of TNFR:Fc fusion protein in phosphate-citrate buffer exhibits less than 5% high and low molecular weight impurities similar to the innovator composition of etanercept comprising phosphate buffer, arginine and sodium chloride after 2 weeks of storage at 40° C. by SEC.

iii. The stable pharmaceutical composition of TNFR:Fc fusion protein in phosphate-citrate buffer, glycine exhibits approximately 8% high and low molecular weight impurities. Whereas the composition of etanercept comprising phosphate buffer, glycine as an anti-aggregating agent showed ~15% impurities, after 2 weeks of storage at 40° C. by SEC.

In another embodiment the invention relates to the pharmaceutical composition of Etanercept in phosphate-citrate buffer with other anti-aggregating agents such as urea, HPBCD.

After obtaining improved stability of Etanercept composition in phosphate-citrate buffer other anti-aggregating agents from other class of compounds than amino acids were tested.

It was observed that Urea and HPBCD also provided stable pharmaceutical compositions of Etanercept in phosphate-citrate buffer. It is understood to mean that etanercept of the pharmaceutical composition does not substantially lose its activity as compared to the composition at the beginning of storage. The term 'substantially' refers to not more than 20%, or more preferably 15%, or even more preferably 10%, and most preferably 5% of its activity relative to activity of the composition at the beginning of storage. The pharmaceutical composition of the invention is suitable for long term storage. As used herein, 'the long term storage' means that the storage of the pharmaceutical composition is stable for more than a month, preferably more than 6 months or 12 months, more preferably more than 24 months.

Tumor Necrosis Factor alpha (TNF-alpha) is a member of a group of cytokines that stimulate the acute phase reaction, and thus is a cytokine involved in systemic inflammation. TNF-alpha is able to induce inflammation, induce apoptotic cell death, and to inhibit tumorgenesis and viral replication. Dysregulation of TNF-alpha production has been implicated in a variety of human diseases like autoimmune disease, ankylosing spondylitis, juvenile rheumatoid arthritis, psoriasis, psoriatic arthritis, rheumatoid arthritis, Wegener's disease (granulomatosis), Crohn's disease or inflammatory bowel disease, chronic obstructive pulmonary disease (COPD), Hepatitis C, endometriosis, asthma, cachexia, atopic dermatitis, Alzheimer as well as cancer.

Dosage of the TNFR:Fc will depend on the disease, severity of condition, patient's clinical history, and response to the (prior) therapy, and will be adjusted and monitored by a physician. The pharmaceutical composition may be administered parenterally, such as subcutaneously, intramuscularly, intravenously, intraperitoneally, intracerebrospinally, intra-articularly, intrasynovially and/or intrathecally by either bolus injection or continuous infusion.

In an embodiment the TNFR:Fc may be administered in adult or juvenile subject, wherein the amount may range from about 1-80 mg. The dose may be administered once weekly, twice weekly. Further, the doses may be administered weekly, biweekly, or separated by several weeks e.g. three weeks. The therapeutic dose and duration may vary as per patient response and patient requirement.

In another embodiment, a suitable regimen for juvenile and paediatric patients may involve a dose of 0.4 mg/kg to 5 mg/kg of TNFR:Fc, administered one or more times per week.

In case of adult rheumatoid arthritis, 25 mg twice weekly or 50 mg once weekly TNFR:Fc may be administered.

In case of psoriatic arthiritis, 25 mg twice weekly or 50 mg once weekly TNFR:Fc may be administered.

In case of Ankolysing spondylitis, 25 mg twice weekly or 50 mg once weekly TNFR:Fc may be administered.

In case of adult plaque psoriasis, the recommended dose of TNFR:Fc is 25 mg administered twice weekly or 50 mg administered once weekly. In case of pediatric plaque psoriasis, the recommended dose of TNFR:Fc is 0.8 mg/Kg weekly with a maximum of 50 mg dose per week.

In case of polyarticular juvenile idiopathic arthritis, the recommended dose of TNFR:Fc is 0.8 mg/Kg weekly with a maximum of 50 mg dose per week.

In case of renal and hepatic impairment no dose adjustment is required.

In a second aspect, the invention relates to a kit comprising a composition according to the first aspect and instructions for use of the present composition.

In a preferred embodiment, the composition is contained in a pre-filled syringe. In another preferred embodiment, the composition is contained in a pre-filled vial. The kit may comprise one or more unit dosage forms containing the pharmaceutical composition of the invention.

Any suitable syringe or vial or cartridge may be used. The kit may also comprise the pharmaceutical composition according to the invention in another secondary container, such as in an autoinjector. The prefilled syringe may contain the composition in aqueous form. Described syringe may be further supplied with an autoinjector, which often is a disposable article for single use only, and may e.g. have a volume between 0.1 and 1 ml. However, the syringe or autoinjector may also be for multi-usage or multi-dosing. The described vial may contain the composition in lyophilised or aqueous state, and may serve as a single or multiple use device. The vial may e.g. have a volume between 1 and 10 ml.

The pharmaceutical composition is sterile and stable for long period of time at 2-8° C. Also it is stable up to 6 months when stored at 25° C. The invention provides pharmaceutical composition essentially comprising of etanercept, phosphate-citrate buffer, anti-aggregating agent selected from L-glycine, urea and HPBCD, a tonicity modifier, a stabilizer and optionally other excipients in suitable combination thereof.

The invention further relates to a stable pharmaceutical composition, wherein the composition is liquid or lyophilized. The invention is further related to a stable pharmaceutical composition in a pre-filled syringe, vial, cartridge, or pen.

In an embodiment of the invention, the active pharmaceutical ingredient etanercept is used which is obtained from recombinant DNA technology using CHO cells. The concentration of the etanercept in the composition is 10 mg/mL to 100 mg/mL. In a preferred embodiment of the invention, the concentration of etanercept in the composition is 10 mg/mL to 60 mg/mL. In the most preferred embodiment of the invention, the concentration of etanercept in the composition is 20 mg/mL to 60 mg/mL.

In another embodiment of the invention, the buffer is phosphate-citrate buffer. In an embodiment of the invention, the concentration of the buffer in the composition is 10 mM to 100 mM. In a preferred embodiment of the invention, the concentration of the buffer in the composition is 10 mM to 50 mM. In another preferred embodiment of the invention, the concentration of the buffer in the composition is 20 mM to 40 mM.

In another embodiment of the invention, the pH of the composition is 5 to 8. In another embodiment of the invention, the etanercept composition comprises anti-aggregating agent selected from L-glycine, urea and HPBCD.

In an embodiment of the invention when the anti-aggregating agent is L-glycine, then the concentration of L-glycine in the composition is 10 mM to 300 mM.

In another embodiment of the invention when the anti-aggregating agent is urea, the concentration of urea in the composition is 20 mM to 50 mM.

In another embodiment of the invention when the anti-aggregating agent is HPBCD, then the concentration of HPBCD is 10 mM to 100 mM.

In another embodiment of the invention, the stable pharmaceutical composition further comprises a parenterally acceptable tonicity agent. The tonicity agent is selected from the group of salts such as sodium chloride, potassium chloride, calcium chloride or saccharides such as mannitol, sucrose, glucose, or amino acids such as arginine, cysteine, histidine and the like. The preferred tonicity agent is sodium chloride. The concentration range varies from 0 mM to 150 mM.

In yet another embodiment of the invention, the stable pharmaceutical composition further comprises a stabilizer. The stabilizer is selected from the group consisting of sucrose, trehalose, lactose, mannitol. The preferred stabilizing agent is sucrose. The concentration of the stabilizing agent in the composition varies from 0.5 wt % to 10 wt %. In the most preferred embodiment of the invention, the concentration of the stabilizer in the composition is 0.5 wt % to 1.5 wt %.

In yet another embodiment of the invention, the stable pharmaceutical composition may optionally comprise a chelating agent. The chelating agent is selected from the group consisting of EDTA, DTPA, HEDTA, NTA and TSP. The preferred chelating agent is EDTA. In a more preferred embodiment of the invention, the concentration of EDTA is 0 mM to 10 mM.

In another embodiment of the invention, the stable pharmaceutical composition of the invention comprises stable etanercept, phosphate-citrate buffer; anti-aggregating agent selected from L-glycine, urea or HPBCD; sucrose as a stabilizing agent and with a long shelf life at temperature 5° C.

In another embodiment of the invention, the stable pharmaceutical composition of the invention comprises stable etanercept, phosphate-citrate buffer; anti-aggregating agent selected from L-glycine, urea or HPBCD; sucrose as a stabilizing agent and with a long shelf life at 5° C.

In another embodiment of the invention, the stable pharmaceutical composition of the invention comprises stable etanercept, phosphate-citrate buffer; anti-aggregating agent selected from L-glycine, urea or HPBCD; sucrose as a stabilizing agent and with 2 weeks shelf life at 40° C.

In another embodiment of the invention, the stable pharmaceutical composition of the invention comprises stable etanercept, phosphate-citrate buffer; anti-aggregating agent selected from L-glycine, urea or HPBCD; sucrose as a stabilizing agent which provides better stability to the pharmaceutical composition to maintain its activity for the longer period of time providing longer shelf life.

In another embodiment, the invention pertains to a method of producing a pharmaceutical composition according to the first aspect, comprising TNFR:Fc, phosphate-citrate buffer, stabilizing agent selected from the group consisting of L-glycine, urea and HPBCD.

In a preferred embodiment, the method may further comprise the step of adding at least one tonicity modifier, such as sodium chloride; a stabilizer, such as sucrose and optionally a chelating agent as defined above.

In another embodiment, the method may further comprise a lyophilization step, which may be before or after adding the at least one tonicity modifier, and/or an excipient as defined above.

Accordingly to a preferred embodiment of the present invention the pharmaceutical composition comprises 10 mg/ml to 100 mg/ml of etanercept, about 10 mM to 100 mM of phosphate citrate buffer, about 10 mM to 300 mM L-glycine, about 0 mM to 150 mM sodium chloride and about 0.5 wt % to 10 wt % sucrose having a pH range of 5 to 7.

Accordingly to another preferred embodiment of the present invention the pharmaceutical composition comprises 10 mg/ml to 100 mg/ml of etanercept, about 10 mM to 100 mM of phosphate citrate buffer, about 1 mg/ml to 18 mg/ml urea, about 1 mM to 150 mM sodium chloride, about 0.5 wt % to 2 wt % sucrose and about 0 mM to 10 mM EDTA having a pH range of 5 to 7.

In another preferred embodiment of the present invention the pharmaceutical composition comprises 10 mg/ml to 100 mg/ml of etanercept, about 10 mM to 100 mM of phosphate citrate buffer, about 20 mg/ml to 30 mg/ml HPBCD, about 1 mM to 150 mM sodium chloride, about 0.5 wt % to 2 wt % sucrose and about 0 mM to 10 mM EDTA having a pH range of 5 to 7.

The invention will be more fully understood by reference to the following examples. However, the examples should not be construed as limiting the scope of the invention.

Experimental Section

The active ingredient etanercept, which was used for the described examples, is derived from recombinant DNA technology in CHO cells. The CHO cells were cultured in a fed-batch process. Etanercept was purified from the cell free harvest by standard purification and filtration process including affinity chromatography and further chromatographic and filtration steps. Etanercept was derived from different production batches which was used in the examples, i.e., example 2 and example 5.

General Process for Preparation of stable pharmaceutical composition of Etanercept The process for preparing the Etanercept drug substance compositions comprises of 2 steps viz. preparation of formulated bulk and fill finish. The formulated bulk is prepared by diluting the drug substance with the formulation buffer to achieve the desired concentration of drug product. The formulation buffer is prepared by adding required quantity of Trisodium Citrate dihydrate and Sodium dihydrogen phosphate dihydrate to WFI followed by mixing. Further, required quantities of other excipients are added to the above solution and the desired volume is adjusted with WFI after adjustment of pH. The formulation buffer is then aseptically filtered using 0.22 µ sterilizing grade PVDF filter. As per the batch calculation, the required quantity of the Etanercept (in same formulation) is aseptically diluted The compositions were analysed by Size Exclusion—High-performance liquid chromatography (SE-HPCL) at different time frames of storage at 5° C., 25° C. and 40° C. SE-HPLC separates the proteins and its related impurities on the basis of their size. Therefore, it is useful to detect aggregation and fragmentation of Etanercept.

The examples which follow are illustrative of the invention and are not intended to be limiting.

EXAMPLE 1

The process for preparing the Etanercept drug substance compositions was comprises of 2 steps viz. preparation of formulated bulk and fill finish. The formulated bulk is prepared by diluting the drug substance with the formulation buffer to achieve the desired concentration of drug product. The formulation buffer is prepared by adding required quantity (as mentioned in table 1) of Trisodium Citrate dihydrate and Sodium dihydrogen phosphate dihydrate to WFI followed by mixing. Further, required quantities of Glycine as anti-aggregating agent and other excipients are added to the above solution and the desired volume is adjusted with WFI after adjustment of pH. The formulation buffer is then aseptically filtered using 0.22 µ sterilizing grade PVDF filter. As per the batch calculation, the required quantity of the Etanercept DS (in same formulation) is aseptically diluted with the filtered formulation buffer to achieve the desired concentration of 50±5 mg/mL of Etanercept bulk. The formulated bulk is filtered through 0.22 µ sterilizing grade PVDF filter and is aseptically dispensed into prefilled syringes. The PFSs were then charged on stability at various temperatures. Table 1 describes the composition obtained using L-glycine as anti-aggregating agent in 75 mM concentration.

TABLE 1

The composition of Example 1

| Excipients | Concentration | Molar Concentration |
|---|---|---|
| Etanercept | 50 mg/mL | 50 mg/mL |
| NaH2PO4 dihydrate | 2.6 mg/mL | 16.6 mM |
| Trisodium Citrate dihydrate | 4.5 mg/mL | 15.3 mM |
| Sucrose | 10 mg/mL | 1% |
| NaCl | 3.8 mg/mL | 65 mM |
| L-glycine | 5.6 mg/mL | 75 mM |

EXAMPLE 2

Etanercept compositions were studied in different buffers and using different anti-aggregating agents. The short term stability of Etanercept composition comprising phosphate-citrate buffer with L-glycine as anti-aggregating agent was analysed at 5° C. for 6 months and 40° C. for 2 weeks along with the Etanercept composition comprising phosphate buffer with L-glycine as anti-aggregating agent, where other excipients were maintained constant by using SE-HPLC and the results are provided in Table 2. The Table 2 illustrates the stability studies of different etanercept compositions.

TABLE 2

Stability studies at 5° C. and 40° C.

| | Etanercept in phosphate citrate buffer with L-glycine | Etanercept in phosphate buffer with L-glycine |
|---|---|---|
| % purity on day 1 @ 5° C. | 92.7 | 91.2 |
| % purity after 6 months @ 5° C. | 85.6 | 68.2 |
| % purity on day 1 @ 40° C. | 90.9 | 89.3 |
| % purity after 2 weeks @ 40° C. | 82.8 | 74.9 |

As table 2 illustrates, Etanercept composition comprising phosphate-citrate buffer with L-glycine as anti-aggregating agent showed improved stability as compared to Etanercept composition comprising phosphate buffer with L-glycine as anti-aggregating agent at 5° C. and 40° C.

EXAMPLE 3

The process for preparing the Etanercept drug substance composition is similar as explained in example 1, wherein the anti-aggregating used is urea. Composition shown in Table 3 was prepared using urea as anti-aggregating agent.

TABLE 3

The composition of Example 3

| Excipients | Concentration | Molar Concentration |
|---|---|---|
| Etanercept | 50 mg/mL | 50 mg/mL |
| NaH2PO4 | 2.6 mg/mL | 16.6 mM |
| Trisodium Citrate | 4.5 mg/mL | 15.3 mM |
| Sucrose | 10 mg/mL | 1% |
| NaCl | 5.8 mg/mL | 100 mM |

TABLE 3-continued

The composition of Example 3

| Excipients | Concentration | Molar Concentration |
|---|---|---|
| EDTA | 1.8 mg/mL | 5 mM |
| Urea | 1.5 mg/mL | 25 mM |

EXAMPLE 4

The process for preparing the Etanercept drug substance composition is similar as explained in example 1, wherein the anti-aggregating used is HPBCD. Composition shown in Table 4 was prepared using HPBCD as anti-aggregating agent.

TABLE 4

The composition of Example 4

| Excipients | Concentration | Molar Concentration |
|---|---|---|
| Etanercept | 50 mg/mL | 50 mg/mL |
| NaH2PO4 | 2.6 mg/mL | 16.6 mM |
| Trisodium Citrate | 4.5 mg/mL | 15.3 mM |
| Sucrose | 10 mg/mL | 1% |
| NaCl | 5.8 mg/mL | 100 mM |
| EDTA | 1.8 mg/mL | 5 mM |
| HPBCD | 25 mg/mL | 17.8 mM |

EXAMPLE 5

The innovator composition of etanercept comprising phosphate buffer and arginine as anti-aggregating agent (Composition 1) and the composition of etanercept comprising phosphate-citrate buffer and L-glycine as anti-aggregating agent (Composition 2) were filled in PFSs and were charged on long term stability which is ongoing. The data of protein purity after 9 months storage at 5° C., 6 months storage at 25° C., 2 weeks storage at 40° C. was analysed by using SE-HPCL and the results are provided in table 5.

TABLE 5

Comparative stability data

| | Composition 1 | Composition 2 |
|---|---|---|
| % purity on day 0 | 97.5 | 97.6 |
| % purity after 9 months @ 5° C. | 96.9 | 96.9 |
| % purity after 6 months @ 25° C. | 94.1 | 93.5 |
| % purity after 2 weeks @ 40° C. | 95.3 | 95.1 |

Similarly, the compositions of example 3 and example 4, i.e., composition of etanercept comprising phosphate-citrate buffer with urea as anti-aggregating agent and composition of etanercept comprising phosphate-citrate buffer with HPBCD as anti-aggregating agent were filled in PFSs and were studied for stability at 5°, 25° and 40° C. The stability of these compositions was assessed and was found comparable with the composition 1 upto period of 2 weeks.

EXAMPLE 6

Etanercept used for the lyophilization studies is formulated and dialyzed extensively with pharmaceutical compositions mentioned in table 6. Respective formulated bulks are filled in vials, half stoppered and are subjected to lyophilization.

TABLE 6

The compositions of Example 6

| Excipients | Composition 3 | Composition 4 |
|---|---|---|
| Etanercept | 50 mg/mL | 50 mg/mL |
| NaH2PO4 dihydrate | 2.6 mg/mL | 2.6 mg/mL |
| Trisodium Citrate dihydrate | 4.5 mg/mL | 4.5 mg/mL |
| Sucrose | 3 mg/mL | 1 mg/mL |
| L-glycine | 11.24 mg/mL | 22.48 mg/mL |

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof.

The invention claimed is:

1. A stable liquid pharmaceutical composition comprising Etanercept, phosphate-citrate buffer, -glycine, sucrose, and sodium chloride.

2. The pharmaceutical composition of claim 1, comprising 10 mg/ml to 100 mg/ml of Etanercept, about 10 mM to 100 mM of phosphate-citrate buffer, about 10 mM to 300 mM glycine, about 50 mM to 120 mM sodium chloride and about 0.5 wt % to 10 wt % sucrose.

3. The stable pharmaceutical composition of claim 1, wherein the composition has a pH in the range of 5 to 7.

4. The stable pharmaceutical composition of claim 1, wherein the composition is sterile and ready for parenteral administration.

5. The pharmaceutical composition of claim 1 comprising 10 mg/ml to 100 mg/ml of Etanercept, about 10 mM to 100 mM of phosphate-citrate buffer, about 10 mM to 300 mM glycine, about 0 mM to 150 mM sodium chloride and about 0.5 wt % to 10 wt % sucrose.

6. The pharmaceutical composition of claim 2 comprising 50 mg/ml of Etanercept, about 16.6 mM of phosphate buffer, about 15.3 mM of citrate buffer, about 75 mM glycine, about 65 mM sodium chloride and about 1 wt % sucrose.

7. The pharmaceutical composition of claim 2 comprising 50 mg/ml of Etanercept, about 31.9 mM of phosphate-citrate buffer, about 75 mM glycine, about 65 mM sodium chloride and about 1 wt % sucrose.

* * * * *